United States Patent
Berry (10) Patent No.: US 7,377,942 B2
(45) Date of Patent: May 27, 2008

(54) POSTERIOR ELEMENTS MOTION RESTORING DEVICE

(75) Inventor: Bret M. Berry, Jacksonville, FL (US)

(73) Assignee: Warsaw Orthopedic, Inc., Warsaw, IN (US)

(*) Notice: Subject to any disclaimer, the term of this patent is extended or adjusted under 35 U.S.C. 154(b) by 348 days.

(21) Appl. No.: 10/635,622

(22) Filed: Aug. 6, 2003

(65) Prior Publication Data
US 2005/0033434 A1 Feb. 10, 2005

(51) Int. Cl.
A61F 2/24 (2006.01)

(52) U.S. Cl. ...................... 623/17.11; 606/61

(58) Field of Classification Search .. 623/17.11–17.16; 606/61, 72, 73
See application file for complete search history.

(56) References Cited

U.S. PATENT DOCUMENTS

| 5,571,191 A | 11/1996 | Fitz |
| 5,609,634 A | 3/1997 | Voydeville |
| 5,645,599 A * | 7/1997 | Samani .................... 623/17.16 |
| RE36,758 E | 6/2000 | Fitz |
| 6,132,464 A | 10/2000 | Martin |
| 6,312,431 B1 | 11/2001 | Asfora |
| 6,419,703 B1 | 7/2002 | Fallin et al. |
| 6,579,319 B2 | 6/2003 | Goble et al. |
| 6,610,091 B1 * | 8/2003 | Reiley ..................... 623/17.11 |
| 6,946,000 B2 * | 9/2005 | Senegas et al. ......... 623/17.11 |
| 6,974,478 B2 * | 12/2005 | Reiley et al. ............ 623/17.11 |
| 2002/0072800 A1 | 6/2002 | Goble et al. |
| 2002/0143331 A1 | 10/2002 | Zucherman et al. |
| 2003/0004572 A1 | 1/2003 | Fallin et al. |
| 2003/0040746 A1 * | 2/2003 | Mitchell et al. .............. 606/61 |
| 2003/0040797 A1 | 2/2003 | Fallin et al. |
| 2004/0116927 A1 * | 6/2004 | Graf ........................... 606/61 |
| 2004/0127989 A1 * | 7/2004 | Dooris et al. ............ 623/13.17 |
| 2005/0010291 A1 * | 1/2005 | Stinson et al. ........... 623/17.11 |

FOREIGN PATENT DOCUMENTS

FR 2 817 461 A1 * 6/2002
WO WO 02/43603 6/2002

* cited by examiner

*Primary Examiner*—Corrine M. McDermott
*Assistant Examiner*—Cheryl Miller
(74) *Attorney, Agent, or Firm*—Haynes and Boone, LLP (57) ABSTRACT

A prosthetic device for interposition in a space left by one or more excised vertebral posterior structures. The prosthetic device comprises a lamina bridge having an inferior portion for replacing an excised lamina; at least one inferior facet replacement device, connected to the inferior portion of the lamina bridge, to replace an excised inferior articular process; and at least one superior facet replacement device to replace an excised superior articular process. The at least one superior facet replacement device articulates with the at least one inferior facet replacement device.

11 Claims, 5 Drawing Sheets

POSTERIOR ELEMENTS MOTION RESTORING DEVICE

FIELD OF THE INVENTION

The present invention relates generally to spinal surgical apparatus, and more particularly, to the replacement of posterior elements of the spine.

BACKGROUND

A variety of injuries and deformities can cause damage to the posterior structures of a vertebrae, which include pedicles, laminae, and articular and spinous processes. To remedy the pain and incapacitation that can be associated with these injuries and deformities, one or more of the posterior vertebral structures may be surgically excised and replaced with a prosthetic device. For example, age, disease or injury, may cause an intervertebral disc to collapse and vertebral bodies to actually make contact. This in turn can cause increased load, wear, damage and resulting pain to one or more joints, such as the facet joints, or to the laminae which may result in the surgical removal of the facets, a facetectomy and/or the laminae, a laminectomy.

Current prosthetic devices used to replace structures removed in a facetectomy or laminectomy can result in either the immobilization at the facet joints or in the alternative extreme, hypermobility in the vertebral column. Therefore, a device is needed to restore more natural motion to the vertebral column after a facetectomy or laminectomy.

SUMMARY

The present disclosure relates to a prosthetic device for interposition in a space left by one or more excised vertebral posterior structures. In one embodiment, the prosthetic device comprises a lamina bridge having an inferior portion for replacing an excised lamina; at least one inferior facet replacement device, connected to the inferior portion of the lamina bridge, to replace an excised inferior articular process; and at least one superior facet replacement device to replace an excised superior articular process. The at least one superior facet replacement device articulates with the at least one inferior facet replacement device.

In another embodiment, a multiple level prosthetic device comprises a first lamina bridge connected to at least one first inferior facet replacement device and a second lamina bridge connected to at least one superior facet extension. The at least one inferior facet replacement device articulates with the at least one superior facet extension.

In another embodiment, at least one translaminar fastener extends through and is connected to a lamina of a first vertebra, and at least one inferior facet replacement device connects to the translaminar fastener.

In another embodiment, the disclosure relates to an apparatus for installing, with minimum invasion into a vertebral column, an articular facet prosthetic device having at least one translaminar fastener and at least one inferior facet replacement device. In this embodiment, the apparatus comprises, a first tubular member for advancing the at least one translaminar fastener into the proximity of a lamina of one vertebra of the vertebral column and extending the at least one translaminar fastener into the lamina. A connective portion of the at least one translaminar fastener extends through the lamina. This embodiment further comprises a second tubular member for connecting the at least one inferior facet replacement to the connective portion of the at least one translaminar fastener.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
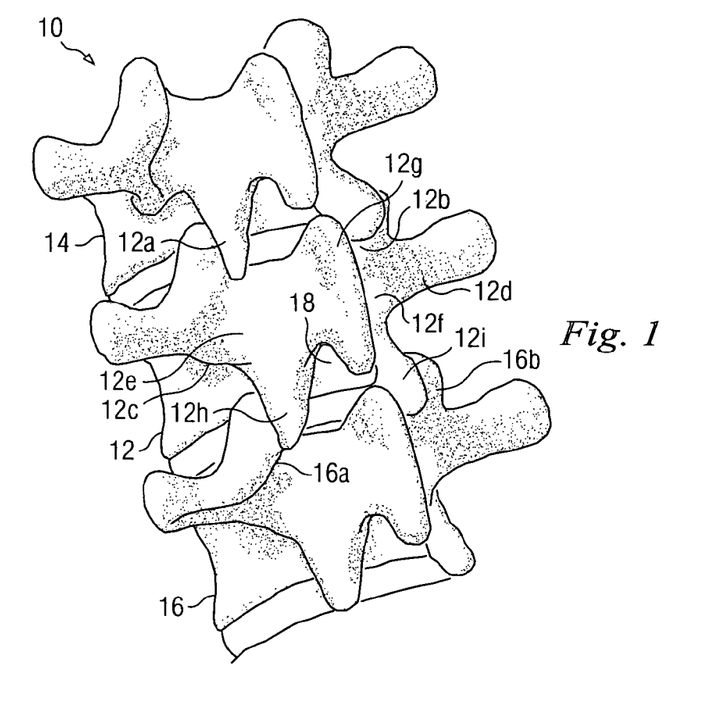
FIG. 1 is an perspective view of a vertebral column having a vertebra with damaged posterior elements.

Referring first to FIG. 1, the reference numeral 10 refers to a vertebral column with a first damaged vertebra 12 extending between a superior vertebra 14 and an inferior vertebra 16. The posterior structures of the damaged vertebra 12 include superior articular facets 12a and 12b supported by pedicles 12c and 12d, a pair of laminae 12e and 12f extending between the pedicles 12c and 12d, a spinous process 12g projecting dorsally from the junction of the laminae 12e and 12f, and inferior articular facets 12h and 12i supported from the junction of the lamina 12e and pedicle 12c and the lamina 12f and pedicle 12d, respectively. These posterior structures span a spinal foramen 18.

In a typical surgical laminectomy, the lamina 12e and 12f are resected together with the spinous process 12g creating a void between the posterior structures of the superior vertebra 14 and the inferior vertebra 16. A surgical facetectomy involves the removal of the inferior articular facets 12h and 12i and may involve the removal of superior articular facets 16a and 16b of the adjacent vertebrae 16. A laminectomy may be performed together with a facetectomy and may involve the removal of the posterior structures of more than one vertebrae. A prosthetic assembly according to an embodiment of the present invention may then be provided to replace one or more of the excised posterior structures.

Figure 2:
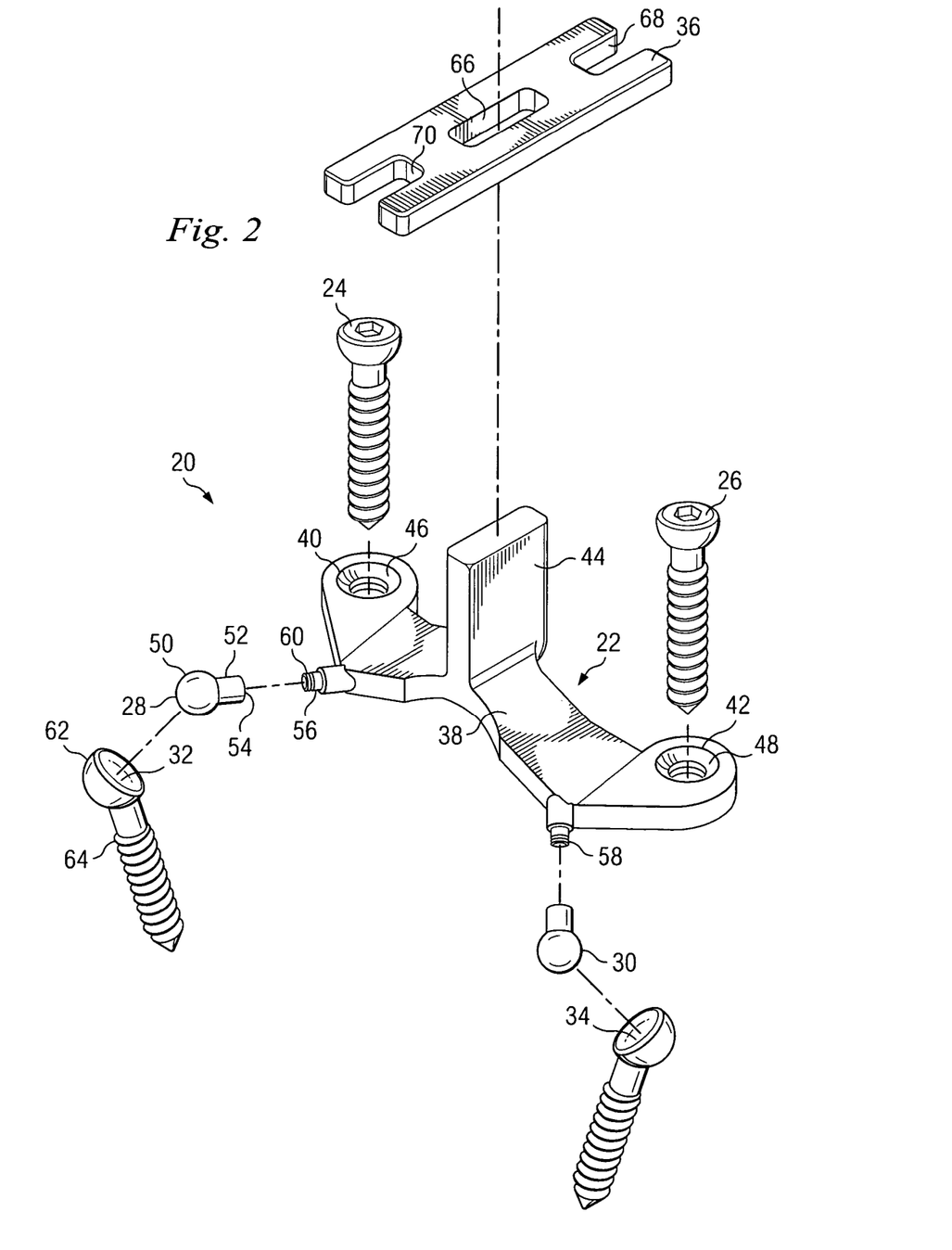
FIG. 2 is an exploded perspective view of a vertebral implant assembly according to one embodiment of the present invention.

Referring now to FIG. 2, a posterior prosthetic assembly according to an embodiment of the present invention may be used following a surgery involving a laminectomy of vertebra 12 (of FIG. 1), an inferior facetectomy of vertebra 12 (of FIG. 1), and a superior facetectomy of vertebra 16 (of FIG. 1). The posterior prosthetic assembly is referred to, in general, by the reference numeral 20 and includes a lamina bridge 22 connected to a pair of pedicle screws 24 and 26, a pair of inferior facet replacement devices 28 and 30, a pair of superior facet replacement devices 32 and 34, and a spinous process bumper 36, all connected in a manner to be described.

The lamina bridge 22, configured to span across the spinal foramen 18 (of FIG. 1), can include a plate 38 having end portions 40 and 42. A spinous process prosthesis 44 may extend dorsally from approximately the center of the plate 38. In some embodiments, the plate 38 may be arched, and in others it may be relatively flat. The lamina bridge 22 may be created from a variety of materials including, for example, titanium, stainless steel, or a radiolucent polymer material such as polyether ether ketone (PEEK™), provided by Victrex PLC of the United Kingdom. Depending upon the material chosen and the amount of motion allowable in the posterior prosthetic assembly 20, the lamina bridge 22 may or may not be rigid.

The end portions 40 and 42 of the lamina bridge 22 may each be provided with threaded apertures 46 and 48, respectively, which are configured to accept the pedicle screws 24 and 26. The pedicle screws 24 and 26 are configured to threadedly engage the pedicles 12c and 12d (of FIG. 1), respectively. In some embodiments, impacted pedicle posts, adhesives or other pedicle connecting mechanisms may be selected as an alternative to pedicle screws. A cover plate (not shown) or any of a variety of devices known in the art may be used to prevent the pedicle screws 24 and 26 from backing out of the pedicle once installed.

The pair of inferior facet replacement devices 28 and 30 are configured to replace inferior articular facets 12h and 12i. In one embodiment, the inferior facet replacement device 28 is detachable which permits the later replacement of a single device 28 without replacing the entire lamina bridge. In this embodiment, the inferior facet replacement device 28 includes a head 50 from which a rod 52 can extend. The head 50 may be spherical or may assume a more anatomical shape to reduce wear and permit a relatively natural range of articulation at the facet joint. At least a portion of the rod 52 may be tubular and carry internal threads 54. A variety of materials may be used separately or together to create the inferior facet replacement device 28 including PEEK™, stainless steel, titanium, cobalt chrome, zirc coatings, and ceramics. The facet devices 28 may also include a spring or other dampening system (not shown) to reduce the wear and shock that might otherwise develop in a semi-constrained joint. The features of the inferior facet replacement device 30 can be similar or identical to the device 28 and therefore, will not be described in detail.

Protruding from the inferior portion of the lamina bridge 22, a pair of inferior facet connectors 56 and 58 may be configured to accept inferior facet replacement devices 28 and 30, respectively. In one embodiment, the connector 56 may have external threads 60 configured to threadedly engage the internal threads 54 of inferior facet replacement device 28. Device 30 may engage connector 58 in a similar or identical manner. Although a threaded connection is described, it is understood that other connection assemblies may be used in alternative embodiments to connect the inferior facet replacement devices 28 and 30 to the lamina bridge 22. Furthermore, although the inferior facet replacement devices 28 and 30 have been described as detachable, it is understood that they may, in alternative embodiments, be a permanent appendage to the lamina bridge 22.

The inferior facet replacement device 28 may articulate with the superior facet replacement device 32 to create an artificial facet joint. The superior facet replacement device 32 may comprise a head 62 from which a stem 64 extends. The stem 64 is configured to fasten to the inferior vertebra 16 and so may, for example, be threaded. The superior facet replacement device 32 may be, for example, a pedicle screw or an impacted pedicle post. The head 62 may be a socket configured to accept the head 50 of the inferior facet replacement device 28, or the configuration of head 62 may be selected from a variety of geometries suitable for engaging the inferior facet replacement device 28. The superior facet replacement device 32 may be created from a variety of materials including titanium, stainless steel, and PEEK™. It is understood that in alternative embodiments, the configuration of the inferior and superior facet replacement devices may be reversed such that the head of the inferior facet replacement device 28 may be configured as a socket to engage a ball-shaped head 62 on the superior facet replacement device 32. The features of the superior facet replacement device 32 can be similar or identical to the device 34 and therefore, will not be described in detail.

The flexible bumper 36 may be attached to the end of the spinous process prosthesis 44 and extend between the spinous processes of the adjacent vertebrae (for example, 14 and 16), cushioning the interface between the spinous process prosthesis 44 and the spinous processes of the adjacent vertebrae. In one embodiment, the bumper 36 can have a center aperture 66 configured to fit over the end of the spinous process prosthesis 44 and a pair of notches 68 and 70 at each end portion configured to engage the adjacent spinous processes. The flexible bumper 36 may be formed from any of a variety of flexible materials including a hydrogel or other elastomers. Once installed, the flexible bumper 36 may permit limited movement in the area of the spinous process without allowing hypermobility which could cause damage to the spinous process and adjacent structures.

Figure 3:
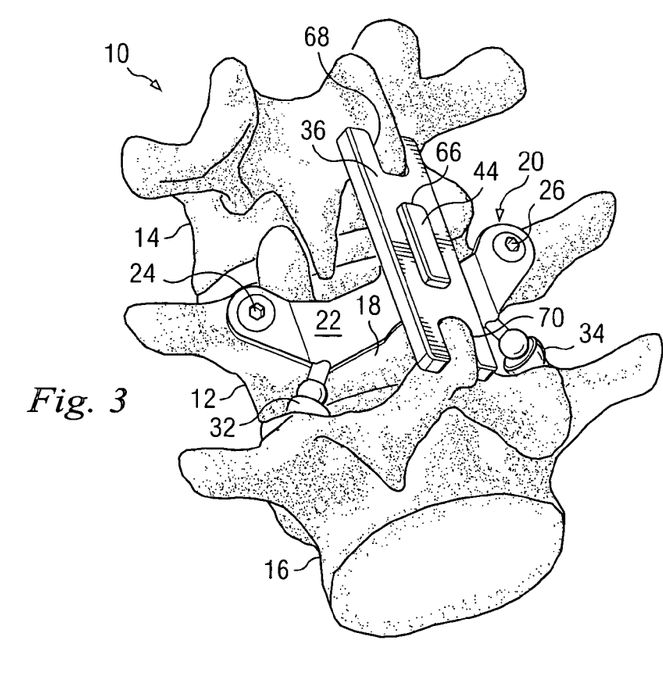
FIG. 3 is a perspective view of the prosthesis of FIG. 2 disposed in a vertebral column.

Referring now to FIG. 3, the vertebral column 10 (of FIG. 1) is shown after a laminectomy of the vertebra 12 and a facetectomy involving the inferior articular facets 12h and 12i of vertebra 12 and the superior articular facets 16a and 16b of the inferior vertebrae 16. Installation of the posterior prosthetic assembly 20 entails surgically embedding the superior facet replacement devices 32 and 34 into the pedicles of vertebra 16, by threading, impacting, or another embedding method known in the art. The lamina bridge 22 can be inserted into the space created by the laminectomy and facetectomy and fastened to the pedicles 12c and 12d using the pedicle screws 24 and 26. It is understood that other types of fasteners such as pedicle posts can be used as an alternative to pedicle screws 24 and 26.

Either before or after the lamina bridge 22 is attached to the vertebra 12, the inferior facet replacement devices 28 and 30 may be threadedly connected to inferior facet connectors 56 and 58, respectively. The inferior facet replacement devices 28 and 30 are then moveably engaged with superior facet replacement devices 32 and 34. The articulating joints formed by the facet replacement devices can restore or maintain motion in the vertebral column 10. As installed, the lamina bridge 22 maintains or increases the original foramen space 18. The aperture 66 in the flexible bumper 36 can then be postioned over the end of the spinous process prosthesis 44 with the notches 68 and 70 in flexible engagement with the spinous processes of vertebrae 14 and 16, respectively.

Figure 4:
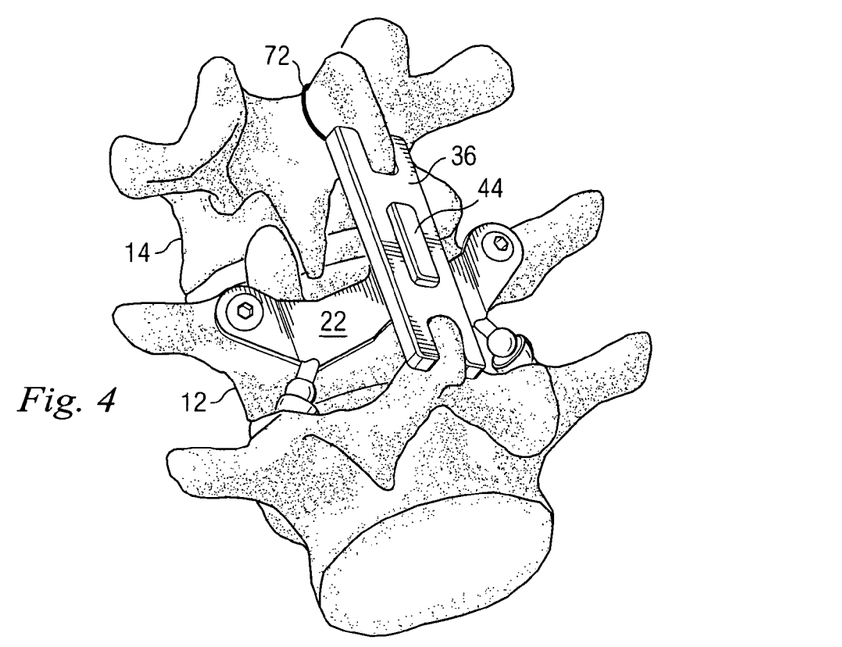
FIG. 4 is a perspective view of a prosthesis disposed within a vertebral column and configured to replace the posterior elements of vertebrae according to a second embodiment of the present invention.

In one embodiment as shown in FIG. 4, an end portion of the flexible bumper 36 may be attached to the spinous process of the adjacent vertebra (e.g., 14 of FIG. 1) with a bumper attachment device 72. The bumper attachment device 72 may be, for example, a cable extending through the flexible bumper 36 and around or through the spinous process of vertebra 14. As needed, a similar bumper attachment device 72 may also or alternatively be used to attach the flexible bumper 36 to the spinous process of vertebra 16. This bumper attachment device 72 can provide additional stabilization of the prosthetic assembly 20 without completely restricting motion in the vertebral column 10.

Figure 5:
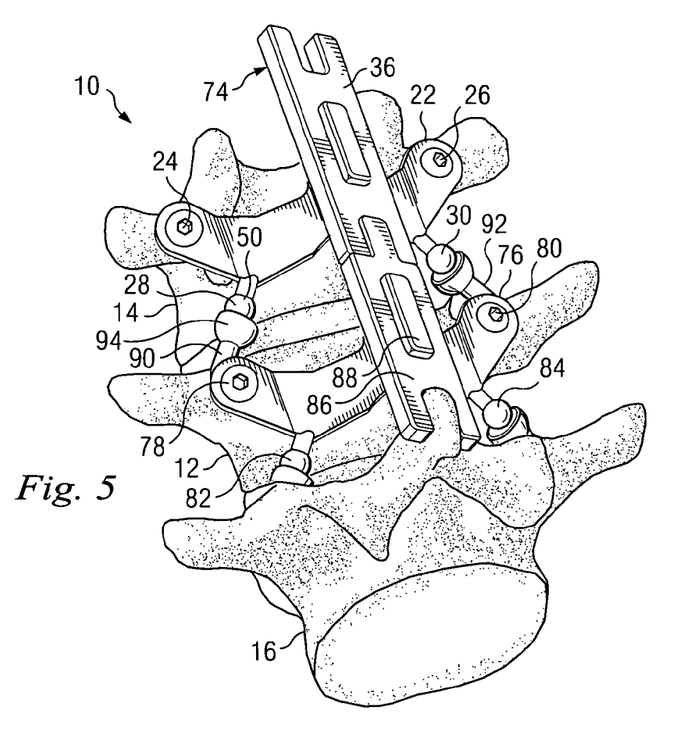
FIG. 5 is a perspective view of a prosthesis disposed within a vertebral column and configured to replace the posterior elements of a vertebrae according to a third embodiment of the present invention.

Referring now to FIG. 5, a multiple level posterior prosthetic assembly 74 can be disposed in a vertebral column 10 (of FIG. 1) following laminectomies of vertebrae 12 and 14 and at least partial facetectomies of vertebra 12, 14, and 16. The multiple level posterior prosthetic assembly 74 can include a first lamina bridge 22 (of FIG. 2); a second lamina bridge 76; two pairs of pedicle screws 24, 26, 78, and 80; two pairs of inferior facet replacement devices 28, 30, 82, and 84; and flexible bumpers 36 and 86. The lamina bridge 76 may include all of the structures described for lamina bridge 22, including a spinous process prosthesis 88 which may extend dorsally from approximately the center of the lamina bridge 76, and may further include a pair of superior facet extensions 90 and 92 protruding from the superior portion of the lamina bridge 76. The extensions 90 and 92 may be aligned to engage the inferior facet replacement devices 28 and 30, respectively. The extension 90 comprises a socket 94 configured for receiving the inferior facet replacement device 28 which may have a spherically or anatomically shaped head 50. In other embodiments, where the head 50 is a socket, the extension 90 may comprise a head configured to engage the socket. The extension 92 may be similar or identical to the extension 90. The lamina bridge 76 and extensions 90 and 92 may be created from a variety of materials including, for example, titanium, stainless steel, or PEEK™.

The flexible bumper 86 of the multiple level posterior prosthetic assembly 74 may be attached to the end of the spinous process prosthesis 88 and extend between the spinous process of vertebra 16 and the flexible bumper 36, cushioning the interface between the spinous process prosthesis 88 and the adjacent natural and artificial spinous processes. In one embodiment, the flexible bumper 86 may comprise an inferior end notch 96 configured to engage the spinous process of vertebra 16. The superior end of the flexible bumper 86 may comprise a protuberance 98 configured to mate with the notch 70 of the flexible bumper 36. The flexible bumper 86 may be formed from any of a variety of flexible materials including a hydrogel or other elastomers. The flexible bumpers 36 and 86 may be further attached to the adjacent spinous processes or artificial spinous processes using the bumper attachment device 72 described above. Alternative embodiments of the multiple level posterior prosthetic assembly 74 may include more than two lamina bridges and associated connective structures.

Figure 6A:
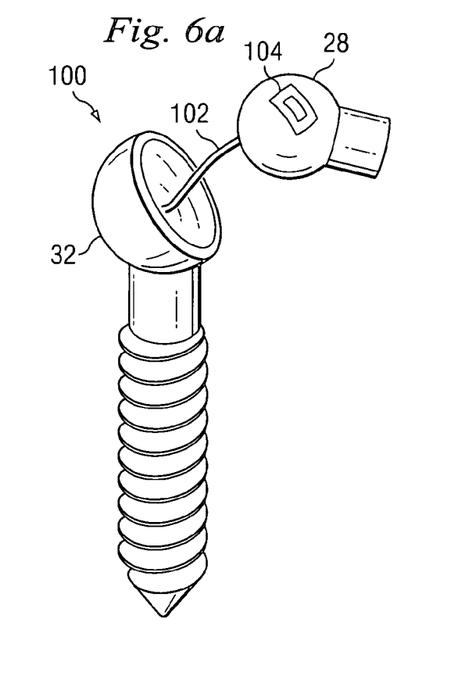
FIG. 6a is an exploded perspective view of a facet replacement assembly having a tether.

Referring now to FIG. 6a, to prevent unnatural motion and reduce wear in the joint formed in FIG. 3 by the inferior facet replacement device 28 and the superior facet replacement device 32, a motion constraint mechanism 100 may be employed. In one embodiment, the motion constraint mechanism 100 may comprise a flexible tether 102 which may extend through both the inferior facet replacement device 28 and the superior facet replacement device 32. An adjustment mechanism 104 may be attached to the tether to hold the tether in place and allow it to become tightened during a surgical procedure.

Figure 6B:
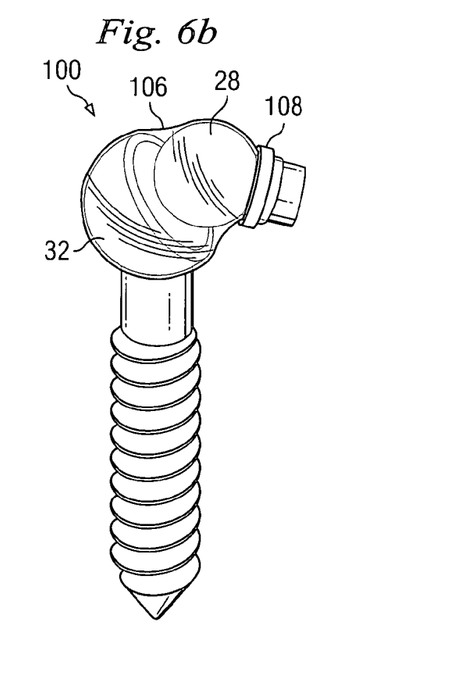
FIG. 6b is an exploded perspective view of a facet replacement assembly having a flexible sheath.

Additionally or alternatively, the motion constraint mechanism 100 may comprise a flexible sheath 106 at least partially surrounding both the inferior facet replacement device 28 and the superior facet replacement device 32. The motion constraint mechanism 100 may include a clamping mechanism 108 to hold the sheath 106 in place. In addition to constraining motion, this sheath 106 can also have the added advantage of containing any wear debris generated at the facet replacement devices.

Further, additionally or alternatively, the joint formed by the inferior facet replacement device 28 and the superior facet replacement device 32 may be at least partially constrained using a hydrogel. A similar or identical motion constraint mechanism 100 can be used at the joint formed by the inferior facet replacement device 30 of FIG. 3 and the superior facet replacement device 34 or any of the joints formed by inferior facet replacement devices, superior facet extensions, or superior facet replacement devices in the multiple level posterior prosthetic assembly 74 of FIG. 5.

Figure 7A:
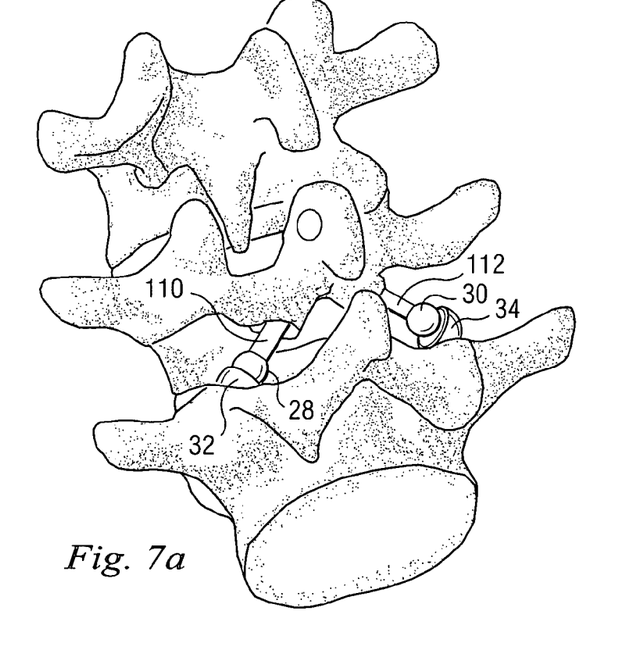
FIG. 7a is a perspective view of a prosthesis disposed within a vertebral column and configured to replace the posterior elements of a vertebra according to a fourth embodiment of the present invention.

Referring now to FIG. 7a, in another embodiment, after a facetectomy of the inferior articular facets 12h and 12i of vertebra 12 and the superior articular facets 16a and 16b of vertebra 16, joint reconstruction may be performed using superior facet replacement devices 32 and 34 (of FIG. 2), inferior facet replacement devices 28 and 30 (of FIG. 2), and translaminar fasteners 110 and 112.

Figure 7B:
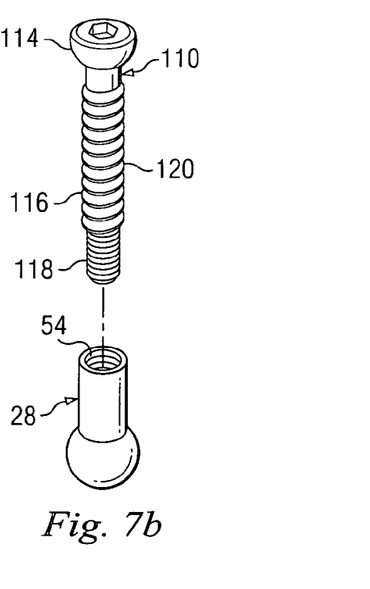
FIG. 7b is an exploded perspective view of a translaminar fastener with a facet replacement device.

As shown in FIG. 7b, the translaminar fastener 110 may, for example, comprise a head 114 and a threaded rod 116. In one embodiment, threads 118 may be formed on the end portion of the threaded rod 116, opposite from the head 114, to engage the internal threads 54 of the inferior facet replacement device 28. The threads 118 may be, for example, machine threads in which case the internal threads 54 of the inferior facet replacement device are also machine threads. A center portion of the threaded rod 116 may have threads 120 which may have a different thread profile from threads 118. The threads 120 may be, for example, bone screw threads. In other embodiments, the threaded rod 116 may be threaded using a single thread profile such as a bone screw thread. The internal threads 54 of the inferior facet replacement device 28 can then also be threaded to accept the single thread profile.

Referring again to FIG. 7a, following the described facetectomies, the translaminar fastener 110 may be threaded into the lamina 12f toward the former location of the inferior articular facet 12h and may continue to advance until at least a portion of the fastener 110 extends into the void created by the removal the inferior articular facet 12h. This procedure may utilize any of a variety of techniques, including, for example, a portion of the Magerl technique for screw placement. The superior facet replacement device 32 can be installed as described above. After the translaminar fastener 110 is threaded through the lamina 12f, the inferior facet replacement device 28 may be threaded onto the translaminar fastener 110. The inferior facet replacement device 28 may then articulate with the superior facet replacement device 32. In some embodiments, the inferior facet replacement device 28 can be connected to the superior facet replacement device 32 while the translaminar fastener 110 is threaded into the inferior facet replacement device 28.

Any of the motion constraint mechanisms 100 described above may also be used in this embodiment.

Translaminar fastener 112 can be similar or identical to translaminar fastener 110 and therefore will not be described in detail. The installation of translaminar fastener 112 may proceed in a manner similar to that described above for translaminar fastener 110, with the fastener 112 threaded through the lamina 12e to engage inferior facet replacement device 30.

Figure 8:
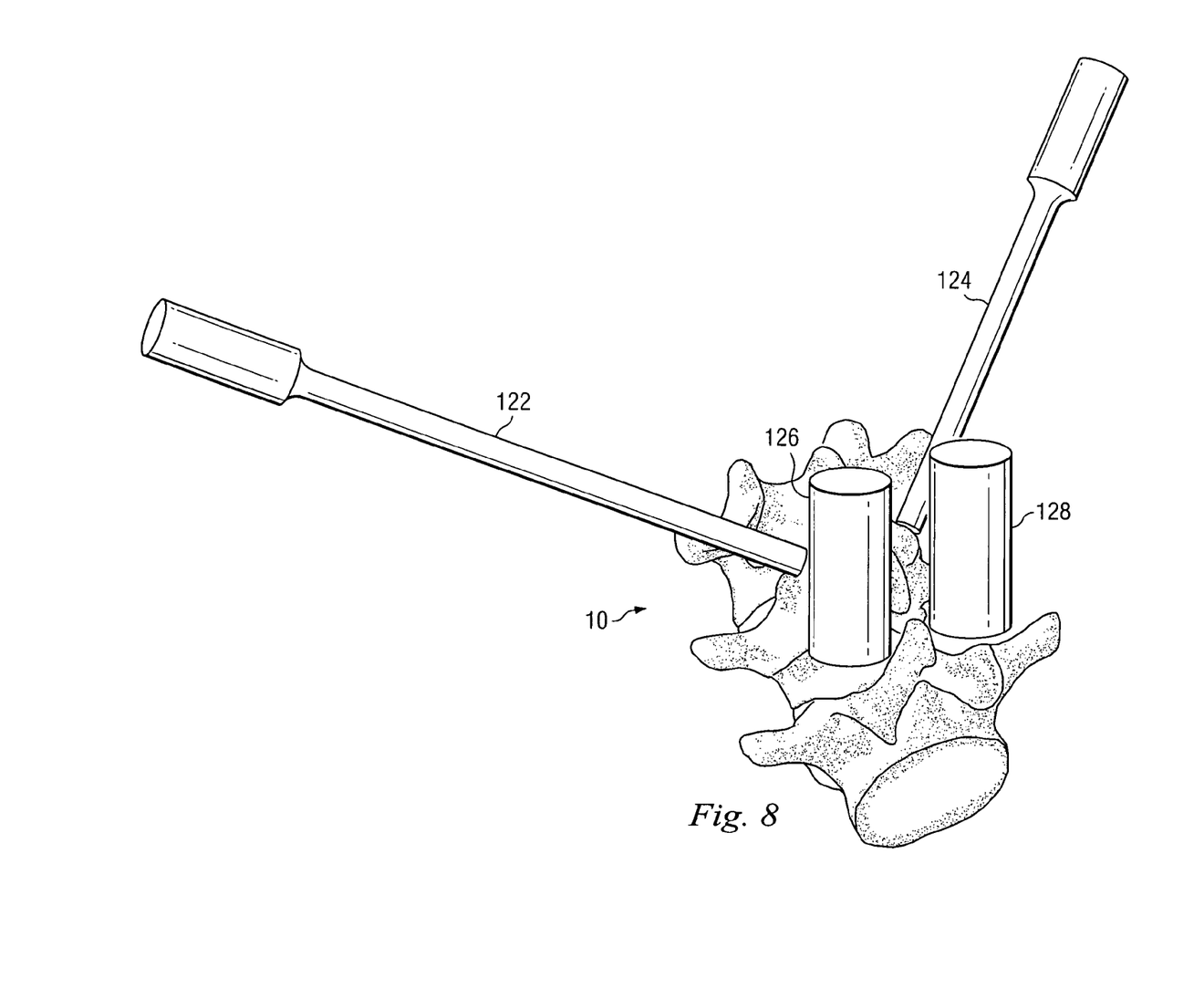
FIG. 8 is a perspective view of an apparatus for installing a prosthesis to replace the posterior elements of a vertebra.

In one embodiment, the joint reconstruction described above may be accomplished using percutaneous, minimally invasive, or image guided techniques to avoid disrupting muscular structures. For example, referring now to FIG. 8, a series of tubes or tubular members may be used to place the translaminar fasteners 110 and 112, the inferior facet replacement devices 28 and 30, and the superior facet replacement devices 32 and 34. A first tube 122, which can have a diameter minimally sized to allow the translaminar fastener 110 through passage, may be inserted percutaneously and extend to the lamina 12e (of FIG. 1). The translaminar fastener 110 may be passed through the first tube 122 to permit installation as described above. The first tube 122 may extend laterally away from the lamina 12e. A similar or identical tube 124 can be used to implant translaminar fastener 112. A second tube 126, which can have a diameter minimally sized to permit through passage of the inferior and superior facet replacement devices 28 and 32, may be inserted percutaneously and extend to the void created by the facetectomy of facets 12h and 16a (of FIG. 1). The inferior and superior facet replacement devices 28 and 32 can be passed through the second tube 126 to permit installation as described above. The second tube 126 may extend dorsally away from the lamina 12e. A similar or identical tube may be used to implant inferior and superior facet replacement devices 30 and 34. The tubes 122, 124, 126, and 128 may be of any length necessary to accommodate installation of the artificial structures. For instance, the first tube 122 may be relatively long whereas the second tube 126 may be relatively short.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A prosthetic device for interposition in a space left by one or more excised vertebral posterior structures, the prosthetic device comprising:
   a lamina bridge connectable to a first vertebra for replacing an excised lamina of the first vertebra wherein the lamina bridge has an inferior portion and comprises a spinous process prosthesis extending dorsally from the lamina bridge;
   at least one inferior facet replacement device, connected to the inferior portion of the lamina bridge;
   a flexible bumper connectable to the lamina bridge via a center aperture of the flexible bumper, the center aperture configured to receive the spinous process prosthesis therein, the flexible bumper having a first end having a notch disposed therein for receiving and moveably connecting with a spinous process of a second vertebra and a second end opposite the first end, the second end having a notch disposed therein for receiving and moveably connecting with a spinous process of a third vertebra, wherein the second and third vertebrae are adjacent the first vertebra; and
   at least one superior facet replacement device,
   wherein the at least one superior facet replacement device articulates with the at least one inferior facet replacement device, and
   wherein a portion of one of the at least one inferior facet replacement device and the at least one superior facet replacement device comprises a majority of a sphere.

2. The prosthetic device of claim 1 wherein the at least one inferior facet replacement device is integrally connected with the lamina bridge.

3. The prosthetic device of claim 1 wherein the at least one inferior facet replacement device is threadedly connected with the lamina bridge.

4. The prosthetic device of claim 1 wherein the at least one inferior facet replacement device comprises a spherical portion in contact with the at least one superior facet replacement device.

5. The prosthetic device of claim 1 further comprising a motion constraint mechanism to control a range of articulation between the at least one inferior facet replacement device and the at least one superior facet replacement device.

6. The prosthetic device of claim 5 wherein the motion constraint mechanism comprises a tether extending between the at least one inferior facet replacement device and the at least one superior facet replacement device.

7. The prosthetic device of claim 5 wherein the motion constraint mechanism comprises a sheath at least partially extended over the at least one inferior facet replacement device and the at least one superior facet replacement device.

8. The prosthetic device of claim 5 wherein the motion constraint mechanism comprises a hydrogel.

9. The prosthetic device of claim 1 wherein the flexible bumper is formed from a hydrogel.

10. The prosthetic device of claim 1 further comprising at least one pedicle screw for securing the lamina bridge to a vertebra.

11. A multiple level prosthetic device for interposition in a space left by the excision of one or more vertebral posterior structures from at least two adjacent vertebrae, the prosthetic device comprising:
   a first lamina bridge for connection to a first vertebra, the first lamina bridge comprising a first spinous process prosthesis extending dorsally from the first lamina bridge, the first lamina bridge connected to at least one inferior facet replacement device; and
   a second lamina bridge connected to at least one superior facet device;
   a first flexible bumper connectable to the first lamina bridge via a center aperture of the flexible bumper, the center aperture configured to receive the spinous process prosthesis therein, the flexible bumper having a first end having a notch disposed therein for receiving and moveably connecting with a spinous process of a second vertebra and a second end opposite the first end, the second end having a notch disposed therein wherein the second vertebrae is adjacent the first vertebra; and
   a second flexible bumper connectable to the second lamina bridge;
   wherein the second end of the first flexible bumper is movably connected to one end of the second flexible bumper such that the first and second flexible bumpers are in direct contact with one another;

wherein the at least one inferior facet replacement device articulates with the at least one superior facet device, and wherein a portion of one of the at least one inferior facet replacement device and the at least one superior facet replacement device comprises a majority of a sphere.

* * * * *